United States Patent [19]

Yoshida et al.

[11] Patent Number: 4,804,762
[45] Date of Patent: Feb. 14, 1989

[54] N-CYANOALKYLISONICOTINAMIDE DERIVATIVES

[75] Inventors: Hiroshi Yoshida, Tokyo; Shizuo Shimano, Ageo; Seiji Mochizuki, Ageo; Kengo Koike, Ageo; Taizo Nakagawa, Omiya; Kenji Konishi, Ageo, all of Japan

[73] Assignee: Nippon Kayaku Kabushiki Kaisha, Tokyo, Japan

[21] Appl. No.: 45,544

[22] Filed: May 4, 1987

[30] Foreign Application Priority Data

May 13, 1986 [JP] Japan .................. 61-107592
Nov. 18, 1986 [JP] Japan .................. 61-272829
Nov. 18, 1986 [JP] Japan .................. 61-272831

[51] Int. Cl.⁴ .............. C07D 407/12; C07D 409/12; A01N 43/40
[52] U.S. Cl. ........................... 514/336; 514/350; 514/354; 546/283; 546/284; 546/298; 546/323
[58] Field of Search ............. 546/283, 284, 298, 323; 514/336, 350, 354

[56] References Cited

U.S. PATENT DOCUMENTS 3,398,155 8/1968 Horrom .................. 546/323

FOREIGN PATENT DOCUMENTS 0172545 2/1986 European Pat. Off. ........... 546/323
2050349 1/1981 United Kingdom ............. 546/323
2095237 9/1982 United Kingdom ............. 549/6

Primary Examiner—Mary C. Lee
Assistant Examiner—Zinna Northington
Attorney, Agent, or Firm—Nixon & Vanderhye

[57] ABSTRACT

Disclosed herein is a compound of the formula:

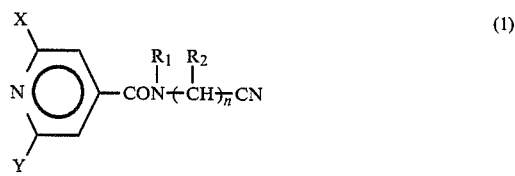

(1)

wherein
X is halogen, lower alkoxy or lower alkylthio,
Y is hydrogen or chloro,
$R_1$ is hydrogen, lower alkyl, cyanomethyl, phenyl or benzyl,
$R_2$ is hydrogen, $C_1 \sim C_7$ - alkyl, $C_3 \sim C_6$ - cycloalkyl, lower alkoxy, phenyl, phenoxyphenyl, furyl, thienyl or benzyl and
n=1 or 2 with a proviso that X and Y are not chloro at the same time, a fungicidal or bactericidal composition containing said compound as an effective component, a method for preventing diseases of agricultural or horticultural plant and a method for manufacturing said compound.

15 Claims, No Drawings

N-CYANOALKYLISONICOTINAMIDE DERIVATIVES

DETAILED DESCRIPTION OF THE INVENTION

This invention relates to a compound of the formula:

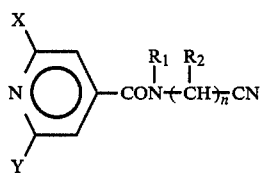

wherein
X is halogen, lower alkoxy or lower alkylthio,
Y is hydrogen or chloro,
$R_1$ is hydrogen, lower alkyl, cyanomethyl, phenyl or benzyl,
$R_2$ is hydrogen, $C_1 \sim C_7$-alkyl, $C_3 \sim C_6$-cycloalkyl, lower alkoxy, phenyl, phenoxyphenyl, furyl, thienyl or benzyl and
n—1 or 2
with a proviso that X and Y are not chloro at the same time, a fungicidal or bactericidal composition containing said compound as an effective component, a method for preventing diseases of agricultural or horticultural plant and a method for manufacturing said compound.

The present invention relates to new N-cyanoalkylisonicotinamide derivatives usable as agricultural and horticultural fungicides or bactericides in paddy fields, upland or orchards.

The prior fungicides include antibiotics, organophosphorus pesticides, synthetic organic fungicides, etc. It is disclosed in Japanese Pat. Laid-Open Nos. 167,978/1982 and 174754/1985 that heterocyclic compounds having a carbamoyl group are useful as fungicides.

Furthermore, in Table on column 3 of U.S. Pat. No. 3,398,155 the compound of the formula:

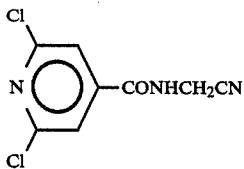

are disclosed. Though the patent says the compound are highly effective as tranquilizer, it never says the compound (A) has any fungicidal or bactericidal activity.

However, the isonicotinamide derivative having one halogen atom in pyridine ring of the present invention is new and there are no suggestions that the compound of the present invention show good fungicidal or bactericidal activity.

The agricultural and horticultural fungicides used heretofore have defects that their effectiveness against rice blast and bacterial diseases such as bacterial leaf blight of rice and angular leaf spot of cucumber is insufficient, that bacteria and fungi resistant to agrochemicals causes trouble, that they are phytotoxic to crops, and that it is not economically advantageous.

The present invention provides useful agricultural and horticultural fungicides free of these defects.

The present inventors have found that when an N-cyanoalkylisonicotinamide derivative represented by the above formula (1) is used, a high controlling effect free of the defects of such prior fungicides is attained, and no adverse effect such as phytotoxicity is caused. The present invention has been completed on the basis of this finding.

The compounds of the formula (1) of the present invention can be produced by a process which comprises reacting an isonicotinoyl chloride of the formula:

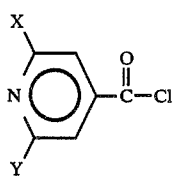

wherein
X is halogen or lower alkoxy or lower alkylthio, and
Y is hydrogen or chloro with the proviso that X and Y are not chloro at the same time,
with a (cyanoalkyl)amine derivative of the formula:

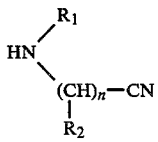

wherein
$R_1$ is hydrogen, lower alkyl, cyanomethyl, phenyl or benzyl,
$R_2$ is hydrogen, $C_1 \sim C_7$-alkyl, $C_3 \sim C_6$-cycloalkyl, lower alkoxy, phenyl, phenoxyphenyl, furyl, thienyl or benzyl and
n is 1 or 2.
in a solvent, occasionally in the presence of an acid-binding agent.

Examples of the acid-binding agents used herein include alkali metal hydroxides such as NaOH and KOH, alkaline earth metal hydroxides such as $Ca(OH)_2$ and $Mg(OH)_2$, alkali metal alcoholates such as sodium alcoholate, alkali metal hydrides such as sodium hydride, alkali metal carbonates such as sodium carbonate and aliphatic and aromatic amines such as trialkylamines, for example, triethylamine, dialkylanilines, for example, dimethyl- and diethyl-anilines and pyridine.

As the solvent, water or organic solvents can be used. Examples of the organic solvents include aromatic hydrocarbons such as benzene, toluene and xylene, aliphatic hydrocarbons such as hexane and heptane, halogenated hydrocarbons such as chloroform and dichloromethane, aprotic polar solvents such as dimethylformamide and dimethyl sulfoxide, ethers such as diethyl ether, tetrahydrofuran and dioxane, nitriles such as acetonitrile and propionitrile, ketones such as acetone and diisopropyl ketone, and esters such as ethyl acetate. The reaction temperature is —10° C. to 100° C., preferably 0° C. to 50° C., and the starting materials are used preferably in an equimolar proportion. On rare occasions, an excess of one of the reaction components may be used favorably.

The crude product is obtained by a usual process, for example, by adding water to the reaction mixture and then by separating the phases. The crude product having a high purity obtained in a high yield can be used as it is or it can be purified by recrystallization or by column chromatography.

The (cyanoalkyl)amines of the formula:

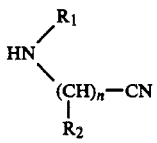
(3)

wherein
$R_1$, $R_2$ and n are as defined above,
can be produced by reacting a corresponding aldehyde with an amine of the formula:

$R_1NH_2$ (4)

wherein
$R_1$ is as defined above,
in the presence of hydrocyanic acid under the Strecker reaction conditions (J. Chem. Soc., 1947, 1371).

The isonicotinamide derivatives of the formula:

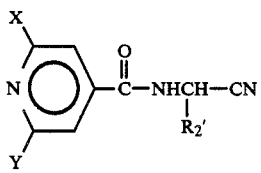
(5)

wherein
X is halogen, lower alkyl or lower alkylthio,
Y is hydrogen or chloro, and
$R_2'$ is lower alkoxy,
can be produced by reacting an N-cyanomethyl-isonicotinamide of the formula:

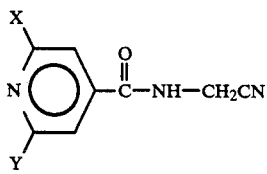
(5)

wherein
X and Y are as defined above,
with a halogenating agent in a solvent to obtain a halogenated intermediate of the formula:

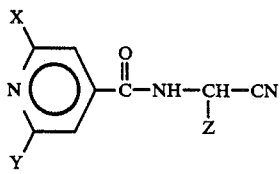
(6)

wherein
X and Y are as defined above, and
Z is a halogen atom, and then reacting the intermediate with an alcohol of the formula:

$R_2'$—H (7)

wherein
$R_2'$ is lower alkoxy, in the presence of an acid-binding agent.

As the solvents for halogenation, aliphatic halides such as dichloromethane, chloroform and carbon tetrachloride are preferred and further, esters such as methyl acetate and ethyl acetate can be used. The preferred halogenating agents are chlorine and bromine. The reaction temperature is 0° to 100° C., preferably 20° to 50° C. Though the halogenated intermediate may be isolated, it is usually reacted directly with the alcohol. This reaction is conducted preferably in the presence of an acid-binding agent. The acid-binding agents include, for example, tertiary amines such as triethylamine, dimethylaniline and pyridine and inorganic bases such as sodium carbonate, potassium carbonate, sodium hydrogencarbonate, sodium hydroxide and potassium hydroxide. The reaction temperature is preferably in the range of −10° to 50° C. The crude product can be purified by recrystallization or silica gel chromatography.

The halogens in the above formula (1) include chlorine, fluorine, bromine and iodine; the lower alkoxy groups include, for example, methoxy, ethoxy, propoxy, isopropoxy and butoxy groups; and the lower alkylthio groups include, for example, methylthio, ethylthio, propylthio and butylthio groups. The lower alkyl groups include, for example, methyl, ethyl, propyl and butyl groups and the alkyl groups having 1 to 7 carbon atoms include, for example, pentyl, hexyl and heptyl groups in addition to the above-mentioned lower alkyl groups. The cycloalkyl groups having 3 to 6 carbon atoms include, for example, cyclopropyl, cyclobutyl and cyclohexyl groups.

Preferred compounds of the present invention are those of the above formula (1) wherein:
X is halogen, lower alkoxy or lower alkylthio,
Y is hydrogen or chloro,
$R_1$ is hydrogen, methyl or benzyl,
$R_2$ is hydrogen, $C_1$~$C_7$-alkyl, $C_3$~$C_6$-cycloalkyl, phenyl, phenoxyphenyl or benzyl,
and n is 1 or 2,
with the proviso that both X and Y are not chlorine atoms at the same time.

Further preferred compounds are those of the above formula (1) wherein:
X is halogen when Y is hydrogen and
X is lower alkoxy or lower alkylthio when Y is chloro,
$R_1$ is hydrogen, methyl or benzyl, and
$R_2$ is hydrogen, $C_1$~$C_7$-alkyl, $C_3$~$C_6$-cycloalkyl, phenyl, phenoxyphenyl or benzyl and
n is 1 or 2.

More preferred compounds are those of the above formula (1) wherein:
X is halogen,
Y is hydrogen,
$R_1$ is hydrogen,
$R_2$ is hydrogen, phenyl, benzyl or cyclohexyl, and
n is 1 or 2.

The most preferred compounds are those of the above formula (1) wherein:
X is halogen,
Y is hydrogen,
$R_1$ is hydrogen,
$R_2$ is hydrogen and n is 1 or 2.

The fungi or bacteria which can be controlled by the compounds of the present invention used as a fungicide or bactericide are, for example, as follows:

*Pyricularia oryzae, Xanthomonas campestris* p.v. *oryzae, Pseudomonas glumae, Pseudomonas lachrymans, Xanthomonas cucurbitae, Xanthomonas campestris* p.v. *campestris, Pseudomonas maculicola, Xanthomonas vitans, Pseudomonas lachrymans, Xanthomonas vescatoria, Pseudomonas solanacearum, Pseudomonas cichorii* and *Xanthomonas vesicatoria.*

One or more of the compounds of the present invention may be used as the active ingredient(s) of an agricultural and horticultural fungicide or bactericide.

According to the purposes of using the compound of the present invention as an agricultural and horticultural fungicide or bactericide, it may be used as it is or, alternatively, a formulation thereof such as dust, microgranule, granule, wettable powder, flowable agent or emulsion with an agricultural adjuvant prepared by a method usually employed in the preparation of pesticides can be used in order to improve or to stabilize their effects.

In the practical use of these various formulations, they may be used either as such or after dilution with water to a desired concentration.

The adjuvants used herein include carriers (diluents) and other adjuvants such as spreaders, emulsifiers, wetting agents, dispersants, fixing agents and disintegrators.

The liquid carriers include aromatic hydrocarbons such as toluene and xylene, alcohols such as methanol, butanol and glycol, ketones such as acetone, amides such as dimethylformamide, sulfoxides such as dimethyl sulfoxide, methylnaphthalene, cyclohexane, animal and vegetable oils, fatty acids and their esters.

The solid carriers include clay, kaolin, talc, diatomaceous earth, silica, calcium carbonate, montmorillonite, bentonite, feldspar, quartz, alumina and saw dust.

As the emulsifier or dispersant, surfactants are usually used. They include anionic, cationic, nonionic and ampnoteric surfactants such as sodium salts of higher alcohol sulfates, stearyltrimethylammonium chloride, polyoxyethylene alkylphenyl ethers and laurylbetaine.

The spreaders include polyoxyethylene nonylphenyl ether and polyoxyethylene lauryl ether; the wetting agents include polyoxyethylene nonylphenyl ether and dialkyl sulfosuccinates; the fixing agents include carboxymethylcellulose and polyvinyl alcohol; and the disintegrators include sodium ligninsulfate and sodium laurylsulfate.

These preparations may be used either alone or in the form of a mixture with other agricultural and horticultural pesticides, insecticides, plant growth regulators and acaricides.

The content of the compound used as the active ingredient of the agricultural and horticultural fungicide of the present invention is variable depending on the type of the preparation, the method of application and other conditions. The active ingredient may be used alone according to circumstances. It is used usually in an amount of 0.5 to 95 wt. %, preferably 2 to 70 wt. %.

Where the composition is applied to the plants, it is preferably sprayed on the leaves and stems in a concentration of the active ingredient of 10 to 4,000 ppm, while in the case of soil application, the amount is preferably 0.05 to 10 kg for 10 acres.

The compounds of the present invention are used as agricultural and horticultural fungicides which exhibit an excellent effect of controlling paddy diseases such as rice blast, bacterial leaf blight of rice and bacterial grain rot of rice and the bacterial diseases such as angular leaf spot of cucumber in the application methods of treating the soil or the locus of the plants, spraying onto the stems and leaves and seed treatment. In addition, they are effective against fungi or bacterial resistant to agrochemicals and exhibit no adverse effect such as phytotoxicity to the plants.

The following examples will further illustrate the present invention.

PREPARATION EXAMPLE 1

Preparation of
N-(2-cyanoethyl)-N-methyl-2-chloroisonicotinamide
(No. 2)

2 g (0.0136 mol) of 2-chloroisonicotinoyl chloride was added dropwise to a solution comprising 1.2 g (0.01136 mol) of N-methyl-N-(2-cyanoethyl)amine, 1.9 ml (0.0136 mol) of triethylamine and 30 ml of acetonitrile under cooling at 5° to 10° C. The mixture was stirred at room temperature for 2 h and then poured into water. Ethyl acetate was added thereto to conduct extraction.

The organic layer was washed with a saturated aqueous common salt solution and dried over anhydrous sodium sulfate. The solvent was distilled off and the resulting crude product was purified according to silica gel column chromatography to obtain 2.1 g (yield: 83.2%) of a light yellow oily product having $n_D^{25}$ of 1.5490.

PREPARATION EXAMPLE 2

Preparation of
N-(2-thienylcyanomethyl)-2-chloroisonicotinamide
(No. 10)

3 g (0.017 mol) of 2-chloroisonicotinoyl chloride was added dropwise to a solution of 2.8 g (0.02 mol) of 2-amino-2-(2-thienyl)acetonitrile and 1.6 g (0.02 mol) of pyridine in 30 ml of toluene while the temperature was kept at 10° to 15° C. The mixture was stirred at room temperature for 1 h. A saturated aqueous common salt solution was added thereto. The organic layer was separated and dried over anhydrous sodium sulfate. The solvent was concentrated under reduced pressure and the crude product was purified according to silica gel column chromatography to obtain 1.5 g (yield: 31.8%) of light brown crystals having a melting point of 123° to 125° C.

PREPARATION EXAMPLE 3

Preparation of
N-(methoxycyanomethyl)-2-chloroisonicotinamide
(No. 6)

4.9 g (0.025 mol) of N-(cyanomethyl)-2-chloroisonicotinamide and 100 ml of dry ethyl acetate were stirred together under heating to dissolve the crystals. Then, dry ethyl acetate containing 4 g (0.025 mol) of bromine was added dropwise thereto while the temperature was kept at 45° to 50° C. After stirring for about 10 min, nitrogen gas was introduced therein. Hydrogen bromide formed was removed and 30 ml of methanol was added to the residue. The resulting mixture was stirred at room temperature for 2 h. A saturated aqueous common salt solution was added thereto and the organic layer was dried over anhydrous sodium sulfate. The solvent was distilled off and the crude product was purified according to silica gel column chromatography to obtain 2.3 g (yield: 40.8%) of light brown crystals having a melting point of 75° to 78° C.

Typical examples of the compounds of the present invention prepared in the same manner as in Preparation Examples 1 to 3 are shown in Table 1.

PREPARATION EXAMPLE 4

Preparation of N-(cyanomethyl)-2-fluoroisonicotinamide (No. 14)

2.4 g (0.056 mol) of sodium hydroxide was dissolved in 24 ml of water. 3.6 g (0.017 mol) of aminoacetonitrile sulfate was added to the solution. 30 ml of ether containing 3.0 g (0.017 mol) of 2-fluoroisonicotinoyl chloride was added dropwise to the solution while the tempera-

TABLE 1

Compounds and physical properties

| No. | $R_1$ | $R_2$ | n | m.p.(°C.) or ($n_D^{25}$) | Appearance |
|-----|-------|-------|---|---------------------------|------------|
| 1 | —$CH_3$ | —H | 1 | (1.5547) | colorless oil |
| 2 | —$CH_3$ | —H | 2 | (1.5490) | light yellow oil |
| 3 | —$C_4H_9(n)$ | —H | 1 | (1.5156) | light brown oil |
| 4 | 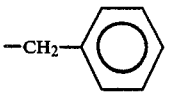 | —H | 2 | (1.5826) | light brown oil |
| 5 | 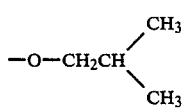 | —H | 2 | (1.5732) | light yellow oil |
| 6 | —H | —$OCH_3$ | 1 | 75–78 | light brown crystals |
| 7 | —H | 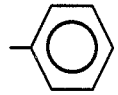 | 1 | 62–65 | light yellow crystals |
| 8 | —H | 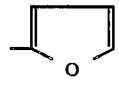 | 1 | 140–142 | light brown crystals |
| 9 | —H | 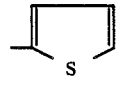 | 1 | 82.5–84.5 | light brown crystals |
| 10 | —H | 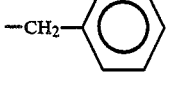 | 1 | 123–125 | light brown crystals |
| 11 | —H | 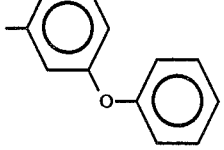 | 1 | 126–127.5 | white crystals |
| 12 | —H |  | 1 | (1.6300) | brown oil |
| 13 | —$CH_2CN$ | H | 1 | (1.5391) | light yellow oil | ture was kept below 5° C. The mixture was stirred at room temperature for 2 h to conduct a reaction. Water and ethyl acetate were added to the mixture to conduct extraction. The organic layer was washed with a saturated aqueous common salt solution and dried over anhydrous sodium sulfate. The solvent was distilled. The resulting crude crystalls were recrystallized from a solvent mixture of n-hexane and ethyl acetate to obtain 2.3 g (yield: 75.3%) of white crystal having a melting point of 124° to 125° C.

PREPARATION EXAMPLE 5

Preparation of N-(cyanomethyl)-2-n-propylthioisonicontinamide (No. 19)

A solution of 2.0 g (0.01 mol) of 2-n-propylthioisonicotinic acid and 1.5 g (0.013 mol) of thionyl chloride in 50 ml of carbon tetrachloride was refluxed for 2 h to conduct a reaction. The solvent was distilled off under reduced pressure to obtain a crude product. 50 ml of ether was added thereto to obtain an acid chloride solution. Separately, 10 ml of an aqueous solution of 1.2 g (0.03 mol) of sodium hydroxide was added dropwise to a solution of 2.1 g (0.01 mol) of aminoacetonitrile sulfate in 10 ml of water at a temperature of 10° C. or below and the mixture was stirred for 30 min. The solution of the acid chloride in ether obtained as above was added dropwise to the latter solution while it was cooled to 0° to 5° C. The mixture was stirred at room temperature for 2 h and then poured into water. After extraction with ethyl acetate, the organic layer was washed with a saturated aqueous common salt solution and dried over anhydrous sodium sulfate. The solvent was distilled off. The resulting crude product was isolated and purified according to silica gel column chromatography to obtain 1.8 g (yield: 74.6%) of a colorless oil having $n_D^{25}$ of 1.5718.

PREPARATION EXAMPLE 6

Preparation of N-(cyanomethyl)-2-chloro-6-n-butoxyisonicotinamide (No. 21)

3.3 g (0.033 mol) of triethylamine was added to a solution of 1.9 g (0.02 mol) of aminoacetonitrile hydrochloride in 30 ml of acetonitrile. The mixture was stirred at room temperature for 30 min. 2.5 g (0.01 mol) of 2-chloro-6-n-butoxyisonicotinoyl chloride was added dropwise thereto under cooling at 5° to 10° C. The mixture was stirred at room temperature for 1 h, poured into water and extracted with ethyl acetate. The extract was washed with a saturated aqueous common salt solution and dried over anhydrous sodium sulfate. The solvent was distilled off under reduced pressure and the crude product was purified according to silica gel column chromatography to obtain 1.9 g (yield: 70.9%) of white crystals having a melting point of 72° to 73° C.

Typical examples of the compounds of the present invention prepared in the same manner as in Preparation Examples 4 to 6 are shown in Table 2.

TABLE 2
Compounds and physical properties $$\begin{array}{c} X \\ \diagdown \\ N \diagup \hspace{-1em}\bigcirc\hspace{-1em} \diagup \hspace{-0.5em} \overset{O}{\underset{\|}{C}} NHCH_2CN \\ \diagup \\ Y \end{array}$$

| No. | X | Y | m.p.(°C.) or ($n_D^{25}$) | Appearance |
|---|---|---|---|---|
| 14 | F | H | 124~125 | white crystals |
| 15 | Br | H | 129.5~130.5 | light brown crystals |
| 16 | I | H | 126~127 | white crystals |
| 17 | SCH₃ | H | 68~71 | light brown crystals |
| 18 | OCH₃ | H | 99~100 | white crystals |
| 19 | SC₃H₇(n) | H | (1.5718) | colorless oil |
| 20 | OCH₃ | Cl | 160~161 | white crystals |
| 21 | OC₄H₉(n) | Cl | 72~73 | white crystals |
| 22 | SCH₃ | Cl | 159~160.5 | white crystals |
| 23 | SC₄H₉(n) | Cl | 97~98 | white crystals |
| 24 | SC₃H₇(i) | H | (1.5640) | light brown oil |

PREPARATION EXAMPLE 7

Preparation of N-(cyanomethyl)-2-chloroisonicotinamide (No. 25)

2.4 g (0.056 mol) of sodium hydroxide was dissolved in 24 ml of water. 3.6 g (0.017 mol) of aminoacetonitrile sulfate was added to the solution and the mixture was stirred at room temperature for 1 h and then cooled to 5° C. or below. A liquid mixture of 3.0 g (0.017 mol) of 2-chloroisonicotinoyl chloride and 30 ml of ether was added dropwise thereto at 5° C. or below lest unfavorable heat generation should occur. The mixture was then stirred at room temperature for 2 h to conduct a reaction. Water and ethyl acetate were added thereto to conduct extraction. The extract was washed with a saturated aqueous common salt solution, dried over anhydrous sodium sulfate and concentrated. The resulting crystals were recrystallized from a liquid mixture of n-hexane and ethyl acetate to obtain 2.7 g (yield: 81.2%) of the intended product as white crystals having a melting point of 131° to 132° C.

PREPARATION EXAMPLE 8

Preparation of N-(1-cyano-2-methylpropyl)-2-chloroisonicotinamide (No. 29)

2.0 g (0.02 mol) of 2-amino-3-methylbutyronitrile and 2.8 ml (0.02 mol) of triethylamine were dissolved in 30 ml of methylene chloride. The solution was cooled to 10° C. or below and 3.0 g (0.017 mol) of 2-chloroisonicotinoyl chloride was added dropwise thereto at 10° C. or below lest unfavorable heat generation should occur. Then, the mixture was stirred at room temperature for 1.5 h to conduct a reaction. Water and ethyl acetate were added thereto to conduct extraction. The extract was washed with water, dried over anhydrous sodium sulfate and concentrated to obtain an oil, which was purified according to silica gel column chromatography to obtain 3.4 g (yield: 84.1%) of the intended product in the form of a colorless oil.

The refractive index $n_D^{25}$ was 1.5276.

Typical examples of the compounds of the present invention prepared in the same manner as in Preparation Examples 7 to 9 are shown in Table 3.

TABLE 3

Compound and Physical properties $$\text{Cl-C}_6\text{H}_3(\text{N})-\text{CONH}-(\text{CH})_n-\text{CN} \text{ with } R_2$$

| No. | $R_2$ | n | m.p. °C. or $(n_D^{25})$ | Appearance |
|---|---|---|---|---|
| 25 | H | 1 | 131~132° C. | white crystals |
| 26 | —CH₃ | 1 | 107~109° C. | light yellow crystals |
| 27 | —CH₂CH₃ | 1 | 70~72° C. | light yellow crystals |
| 28 | —CH₂CH₂CH₃ | 1 | 86~88° C. | light yellow crystals |
| 29 | —CH(CH₃)₂ | 1 | (1.5276) | colorless oil |
| 30 | —C₆H₁₁ (cyclohexyl) | 1 | 125~126° C. | white crystals |
| 31 | —CH(CH₃)CH₂CH₂CH₃ | 1 | (1.5275) | light brown oil |
| 32 | —(CH₂)₆CH₃ | 1 | (1.5180) | light yellow oil |
| 33 | H | 2 | 113~114.5° C. | white crystals |

The formulations are illustrated by the following Examples in which parts are given by weight, but the kinds and mixing proportions of agricultural adjuvants are not limited thereby and may be widely varied.

FORMULATION EXAMPLE 1

Dust 2 parts of Compound No. 3 was mixed with 98 parts of clay and the mixture was pulverized to obtain a dust.

FORMULATION EXAMPLE 2

Wettable powder 20 parts of Compound No. 24, 75 parts of kaolin, 3 parts of sodium salt of a higher alcohol sulfate and 2 parts of sodium ligninsulfonate were mixed together and pulverized to obtain a wettable powder.

FORMULATION EXAMPLE 3

Granules 8 parts of finely pulverized Compound No. 8, 36 parts of diatomaceous earth, 24 parts of bentonite, 30 parts of talc and 2 parts of a disintegrator were mixed together. 18 parts of water were added to the mixture to wet it uniformly. The mixture was extruded by means of an injection molding machine to form granules. The granules were sized in a sizing machine and dried to obtain granules having a diameter of 0.6 to 1 mm.

FORMULATION EXAMPLE 4

Microgranules 5 parts of Compound No. 25 was dissolved in 5 parts of methanol. The solution was added dropwise to 95 parts of 80- to 250-mesh granular clay under stirring. The mixture was dried to obtain microgranules.

FORMULATION EXAMPLE 5

Emulsion 30 parts of Compound No. 1 were dissolved in 52 parts of xylene. The solution was mixed with 18 parts of a mixture of an alkylphenol-ethylene oxide condensate and a calcium alkylbenzenesulfonate (8:2) to obtain an emulsion.

This emulsion is to be diluted with water to obtain a dilute emulsion when it is used.

The excellent effects of controlling various diseases of agricultural and horticultural crops exhibited by the compounds of the present invention are illustrated by the following Experimental Examples.

EXPERIMENTAL EXAMPLE 1

Tests of controlling rice blast by submerged application

A rice plant (variety: Saitama-Mochi X) was raised in each plastic pot having a size of 11 cm×5 cm×10 cm for 2 weeks. A given amount of granules containing the compound of the present invention prepared in Formulation Example 3 as the active ingredient was applied to the soil in the pot. After 7 days, leaves of the rice plant were inoculated with *Pyricularia oryzae* by spraying its spore suspension. After keeping them in a humid chamber at 23° C. for 2 days, the disease was further developed in a greenhouse. The symptoms of the disease were observed 10 days after the inoculation, and the control index was calculated by the formula below. The results are shown in Table 4. IBP granul (active ingredient: S-benzyldiisopropyl phosphorothiolate) was used as the control.

| Degree of Disease | Results observed |
|---|---|
| 0 | no disease specks |
| 1 | slight disease specks |
| 2 | many disease specks |
| 3 | extremely many disease specks, and only some blighted leaves |
| 4 | many blighted leaves |
| 5 | extremely many blighted leaves |

$$\text{Control Index} = \frac{\left(\begin{array}{c}\text{Degree of disease in}\\\text{the untreated plot}\end{array}\right) - \left(\begin{array}{c}\text{Degree of disease in}\\\text{the treated plot}\end{array}\right)}{(\text{Degree of disease in the untreated plot})} \times 100$$

TABLE 4

Tests of controlling rice blast (submerged application)

| Tested compound | | Amount of active ingredient, mg/pot | Control index | Phytotoxicity |
|---|---|---|---|---|
| Compound No. of the present invention | 1 | 20 | 89 | none |
| | 7 | 20 | 81 | none |
| | 8 | 20 | 88 | none |
| | 11 | 20 | 87 | none |
| | 14 | 20 | 90 | none |
| | 15 | 20 | 86 | none |
| | 17 | 20 | 81 | none |
| | 18 | 20 | 89 | none |
| | 19 | 20 | 80 | none |
| | 25 | 20 | 89 | none |
| | 26 | 20 | 78 | none |
| | 27 | 20 | 80 | none |
| | 28 | 20 | 77 | none |

TABLE 4-continued

Tests of controlling rice blast (submerged application)

| Tested compound | Amount of active ingredient, mg/pot | Control index | Phytotoxicity |
|---|---|---|---|
| 29 | 20 | 78 | none |
| 30 | 20 | 79 | none |
| 31 | 20 | 75 | none |
| 33 | 20 | 89 | none |
| Control IBP granules | 20 | 65 | none |

EXPERIMENTAL EXAMPLE 2

Test of controlling rice blast by foliar spray

A rice plant (variety: Saitama-Mochi X) was raised in each plastic pot having a size of 1 cm×5 cm×10 cm for 2 weeks. A liquid preparation of a given concentration obtained by diluting a wettable powder containing a compound of the present invention prepared in Formulation Example 2 as the active ingredient was sprayed on the stems and leaves of the rice plant. After air-dried, the plant was inoculated with a spore suspension of *Pyricularia oryzae* by spray. After keeping it in a humid chamber at 23° C. for 2 days, the disease was developed in a greenhouse. The degree of the symptoms was observed 10 days after the inoculation, and the control index was calculated according to the formula given below. The results are shown in Table 5. An IBP emulsion (active ingredient: S-benzyldiisopropyl phosphorothiolate) was used as a control.

| Degree of disease | Results observed |
|---|---|
| 0 | no disease specks |
| 1 | slight disease specks |
| 2 | many disease specks |
| 3 | extremely many disease specks, and only some blighted leaves |
| 4 | many blighted leaves |
| 5 | extremely many blighted leaves |

Control Index =

$$\frac{\left(\begin{array}{c}\text{Degree of disease in}\\\text{the untreated plot}\end{array}\right) - \left(\begin{array}{c}\text{Degree of disease in}\\\text{the treated plot}\end{array}\right)}{(\text{Degree of disease in the untreated plot})} \times 100$$

TABLE 5

Tests of controlling rice blast of rice (foliar spray)

| Tested compound | Concentration of active ingredient, ppm | Control index | Phytotoxicity |
|---|---|---|---|
| Compound No. of the present invention 11 | 200 | 69 | none |
| 14 | 200 | 70 | none |
| 15 | 200 | 71 | none |
| 18 | 200 | 69 | none |
| 25 | 200 | 70 | none |
| 26 | 200 | 67 | none |
| 33 | 200 | 70 | none |
| Control IBP granules | 200 | 60 | none |

EXPERIMENTAL EXAMPLE 3

Tests of controlling bacterial leaf blight of rice by submerged application

A rice plant (variety: Musashi-kogane) was raised in each plastic pot having a size of 15 cm×5 cm×10 cm for 1.5 months. Granules of the compound of the present invention prepared in Formulation Example 3 were applied to the soil in the pot in a given amount. After two days, the leaves of the rice plant were inoculated with *Xanthomonas campestris* p.v. *oryzae*. After keeping them in a humid chamber at 30° C. for 24 hr, the disease was further developed in a greenhouse. The length of the disease specks of the leaf was examined 21 days after the inoculation.

The results are shown in Table 6. Probenazol granules (active ingredient: 1,2-benzisothiazol-3-one 1,1-dioxide) were used as the control.

TABLE 6

Tests of controlling bacterial leaf blight of rice by submerged application

| Tested compound | Amount of active ingredient (mg/pot) | Average length of disease specks | Phytotoxicity |
|---|---|---|---|
| Compound No. of the present invention 2 | 10 | 4.7 | none |
| 3 | 10 | 4.2 | none |
| 4 | 10 | 4.3 | none |
| 5 | 10 | 4.6 | none |
| 6 | 10 | 4.2 | none |
| 9 | 10 | 4.3 | none |
| 11 | 10 | 4.3 | none |
| 14 | 10 | 4.1 | none |
| 15 | 10 | 3.8 | none |
| 17 | 10 | 4.0 | none |
| 18 | 10 | 4.1 | none |
| 19 | 10 | 4.4 | none |
| 20 | 10 | 4.4 | none |
| 23 | 10 | 4.7 | none |
| 24 | 10 | 4.5 | none |
| 30 | 10 | 4.8 | none |
| Control Probenazol granules | 10 | 5.2 | none |
| Untreated | — | 12.0 | — |

EXPERIMENTAL EXAMPLE 4

Tests of controlling angular leaf spot of cucumber by foliar spray

A solution having a given concentration prepared by diluting the wettable powder of the compound of the present invention prepared in Formulation Example 2 was sprayed on the stems and leaves of a cucumber plant (variety: Suyo) of a 4 leaves stage raised in each plastic pot having a diameter of 10 cm. After two days, suspension of angular leaf spot was sprayed on the cucumber leaves. The plant was kept in an inoculation box at 25° C. for 2 days and the disease was developed in a greenhouse. The area of the disease specks was examined 10 days after the inoculation. The results were evaluated according to the following criteria:

| Criteria | Results observed |
|---|---|
| 0 | disease speck area: more than 70% |
| 1 | disease speck area: 40 to 70% |
| 2 | disease speck area: 10 to 40% |
| 3 | disease speck area: less than 10% |

The results are shown in Table 7. A copper-based wettable powder (active ingredient: cupric hydroxide) was used as the control.

TABLE 7

Tests of controlling *Pseudomonas lachrymans* of cucumber by foliar spray

| Tested compound | | Conc. of active ingredient, ppm | Control index | Phytotoxicity |
|---|---|---|---|---|
| Compound No. of the present invention | 15 | 500 | 3 | none |
| | 25 | 500 | 3 | none |
| | 33 | 500 | 3 | none |
| Control | Copper-based wettable powder | 800 | 1 | none |

What we claim is:

1. A compound of the formula:

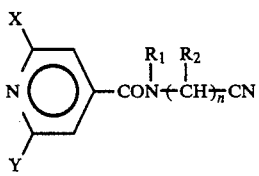

(1)

wherein

X is halogen, lower alkoxy or lower alkylthio,

Y is hydrogen or chloro; with the proviso that X is halogen, lower alkoxy or lower alkylthio when Y is hydrogen and X is lower alkoxy or lower alkylthio when Y is chloro;

$R_1$ is hydrogen, lower alkyl, cyanomethyl, phenyl or benzyl;

$R_2$ is hydrogen, $C_1$–$C_7$-alkyl, $C_3$–$C_6$-cycloalkyl, lower alkoxy, phenyl, phenoxyphenyl, furyl, thienyl or benzyl; and n is 1 or 2.

2. A compound according to claim 1, wherein

X is halogen, lower alkoxy or lower alkylthio when Y is hydrogen and X is lower alkoxy or lower alkylthio when Y is chloro;

$R_1$ is hydrogen, methyl or benzyl;

$R_2$ is hydrogen, $C_1$–$C_7$ alkyl, $C_3$–$C_6$-cycloalkyl, phenyl, phenoxyphenyl or benzyl; and n is 1 or 2.

3. A compound according to claim 1, wherein

X is halogen when Y is hydrogen, X is lower alkoxy or lower alkylthio when Y is chloro, $R_1$ is hydrogen, methyl or benzyl, $R_2$ is hydrogen, $C_1$~$C_7$-alkyl, $C_3$~$C_6$-cycloalkyl, phenyl, phenoxyphenyl or benzyl and n is 1 or 2.

4. A compound of claim 3, wherein,

X is halogen,

Y is hydrogen, $R_1$ is hydrogen, $R_2$ is hydrogen, phenyl, benzyl or cyclohexyl, and n is 1 or 2.

5. A compound according to claim 4, wherein

X is halogen,

Y is hydrogen, $R_1$ is hydrogen, $R_2$ is hydrogen and n is 1 or 2.

6. A fungicidal or bactericidal composition which comprises an effective amount of a compound of the formula:

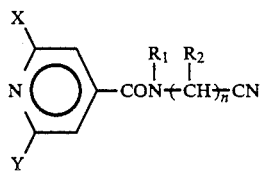

(1)

wherein

X is halogen, lower alkoxy or lower alkylthio,

Y is hydrogen or chloro, $R_1$ is hydrogen, lower alkyl, cyanomethyl, phenyl or benzyl, $R_2$ is hydrogen, $C_1$~$C_7$-alkyl, $C_3$~$C_6$-cycloalkyl, lower alkoxy, phenyl, phenoxyphenyl, furyl, thienyl or benzyl and n = 1 or 2 with a proviso that X and Y are not chloro at the same time, as an effective component and adjuvant(s).

7. A fungicidal or bactericidal composition according to claim 6, wherein

X is halogen, lower alkoxy or lower alkylthio,

Y is hydrogen or chloro, $R_1$ is hydrogen, methyl or benzyl, $R_2$ is hydrogen, $C_1$~$C_7$-alkyl, $C_3$~$C_6$-cycloalkyl, phenyl, phenoxyphenyl or benzyl and n is 1 or 2, with the proviso X and Y are not chloro at the same time.

8. A fungicidal or bactericidal composition according to claim 6, wherein

X is halogen when Y is hydrogen,

X is lower alkoxy or lower alkylthio when Y is chloro, $R_1$ is hydrogen, methyl or benzyl, $R_2$ is hydrogen, $C_1$~$C_7$-alkyl, $C_3$~$C_6$-cycloalkyl, phenyl, phenoxyphenyl or benzyl and n is 1 or 2.

9. A fungicidal or bactericidal composition according to claim 8,

X is halogen,

Y is hydrogen, $R_1$ is hydrogen, $R_2$ is hydrogen, phenyl, benzyl or cyclohexyl, and n is 1 or 2.

10. A fungicidal or bactericidal composition according to claim 9, wherein

X is halogen,

Y is hydrogen, $R_1$ is hydrogen, $R_2$ is hydrogen and n is 1 or 2.

11. A method for preventing diseases of agricultural or horticultural plants caused by fungi or bacteria which comprises applying to soil, said plants or locus thereof a fungicidally or bacteriocidally effective amount of the compound of the formula:

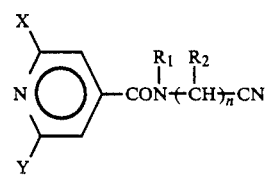

(1)

wherein
- X is halogen, lower alkoxy or lower alkylthio,
- Y is hydrogen or chloro,
- $R_1$ is hydrogen, lower alkyl, cyanomethyl, phenyl or benzyl,
- $R_2$ is hydrogen, $C_1 \sim C_7$-alkyl, $C_3 \sim C_6$-cycloalkyl, lower alkoxy, phenyl, phenoxyphenyl, furyl, thienyl or benzyl and n=1 or 2 with a proviso that X and Y are not chloro at the same time.

12. A method according to claim 11, wherein
- X is halogen, lower alkoxy or lower alkylthio,
- Y is hydrogen or chloro,
- $R_1$ is hydrogen, methyl or benzyl,
- $R_2$ is hydrogen, $C_1 \sim C_7$-alkyl, $C_3 \sim C_6$-cycloalkyl, phenyl, phenoxyphenyl or benzyl and
- n is 1 or 2, with the proviso X and y are not chloro at the same time.

13. A method according to claim 11, wherein
- X is halogen when Y is hydrogen,
- X is lower alkoxy or lower alkylthio when Y is chloro,
- $R_1$ is hydrogen, methyl or benzyl,
- $R_2$ is hydrogen, $C_1 \sim C_7$-alkyl, $C_3 \sim C_6$-cycloalkyl, phenyl, phenoxyphenyl, benzyl and
- n is 1 or 2.

14. A method of claim 13, wherein,
- X is halogen,
- Y is hydrogen,
- $R_1$ is hydrogen,
- $R_2$ is hydrogen, phenyl, benzyl or cyclohexyl,
- n is 1 or 2.

15. A method according to claim 14, wherein,
- X is halogen,
- Y is hydrogen,
- $R_1$ is hydrogen,
- $R_2$ is hydrogen and
- n is 1 or 2.

* * * * *